US007668291B2

(12) United States Patent
Nord et al.

(10) Patent No.: US 7,668,291 B2
(45) Date of Patent: Feb. 23, 2010

(54) LEAF SEQUENCING

(75) Inventors: Janne Ilmari Nord, Espoo (FI); Sami Pekka Siljamäki, Espoo (FI); Katja Marika Pesola, Vantaa (FI)

(73) Assignee: Varian Medical Systems International AG, Zug (CH)

( * ) Notice: Subject to any disclaimer, the term of this patent is extended or adjusted under 35 U.S.C. 154(b) by 37 days.

(21) Appl. No.: 11/804,693

(22) Filed: May 18, 2007

(65) Prior Publication Data

US 2008/0285719 A1   Nov. 20, 2008

(51) Int. Cl.
    *A61N 5/10*   (2006.01)
(52) U.S. Cl. .......................................... 378/65; 378/152
(58) Field of Classification Search .................. 378/65, 378/145–153, 901
    See application file for complete search history.

(56) References Cited

U.S. PATENT DOCUMENTS

| 5,818,902 | A * | 10/1998 | Yu ............................... 378/65 |
| 6,907,105 | B2 | 6/2005 | Otto |
| 7,162,008 | B2 | 1/2007 | Eart et al. |
| 7,333,591 | B2 | 2/2008 | Earl et al. |
| 2004/0184578 | A1 | 9/2004 | Nakano |
| 2006/0256915 | A1 | 11/2006 | Otto et al. |
| 2008/0144772 | A1 | 6/2008 | Yi et al. |
| 2008/0226030 | A1 | 9/2008 | Otto |
| 2008/0298550 | A1 | 12/2008 | Otto |

FOREIGN PATENT DOCUMENTS

| WO | WO 00/07668 A1 | 2/2000 |
| WO | 2008011725 A1 | 1/2008 |

OTHER PUBLICATIONS

Daliang Cao et al., Continuous intensity map optimization (CIMO): A novel approach to leaf sequencing in step and shoot IMRT, Medical Physics, Apr. 2006, 859-867, vol. 33 No. 4, American Association of Physicists in Medicine.
M A Earl et al., Inverse planning for intensity-modulated arc therapy using direct aperture optimization, 2003, 1075-1089, vol. 48, IOP Publishing Ltd, UK.
D.M. Shepard et al, An arc-sequencing algorithm for intensity modulated arc therapy, Feb. 2007, 464-470, vol. 34 No. 2, American Association of Physicists in Medicine.
Chao Wang et al., "Arc-modulated radiation therapy (AMRT): a single-arc form of intensity-modulated arc therapy"; Phys. Med. Biol., 2008, pp. 6291-6303, vol. 53, Institute of Physics and Engineering in Medicine, Printed in UK.

* cited by examiner

*Primary Examiner*—Courtney Thomas
(74) *Attorney, Agent, or Firm*—Gard & Kaslow LLP

(57) ABSTRACT

Systems and methods of controlling the leaves of an aperture in radiation treatment are disclosed. In some embodiments, these systems and methods allow the delivery of different radiation fluences to different parts of a treatment volume in a single rotation of the aperture around the treatment volume. In some embodiments, different radiation fluences are achieved by radiating different parts of the treatment volume from opposing positions of the aperture around the treatment volume. In some embodiments, different radiation fluences are achieved by assigning different leaf pairs to radiate different parts of the treatment volume.

31 Claims, 14 Drawing Sheets

LEAF SEQUENCING

BACKGROUND

1. Field of the Invention

The invention is in the field of radiation therapy and more specifically related to the use of leaf apertures to control delivery of radiation to a patient.

2. Related Art

Radiation, e.g., x-rays or particle beams, is used in a variety of medical treatments. Preferably, radiation is delivered to a treatment volume and not to a surrounding region of healthy tissue. In order to achieve these treatment preferences, a radiation beam is typically shaped using an aperture. The aperture is configured to shape the radiation beam according to a geometric projection of the treatment volume along the axis of the radiation beam.

One type of aperture includes a series of movable leaves. These leaves may be comprised of a series of thin plates whose thin dimension and axis of movement are both perpendicular to the direction of the radiation beam. Movement of the leaves allows for the generation of a variety of openings and, thus, a variety of radiation beam shapes. The resolution of these shapes is, in part, dependent on the thickness and number of the plates.

In some treatment schemes, a radiation source and aperture are rotated around the treatment volume, i.e., around a patient, using a gantry. One advantage of this approach is that the radiation beam does not always pass through the same healthy tissue. For example, at two different points in the rotation process, the radiation beam may be directed at the treatment volume from directions that differ by approximately ninety degrees. While the radiation beam passes through the treatment volume from both directions, it passes through different parts of the healthy tissue from the different directions. As such, the harmful impacts on the healthy tissue are distributed and their total magnitude reduced.

In the prior art, the rotating radiation source and aperture are configured to provide a single fluence. The fluence is a two-dimensional object defined in a plane. An intensity is defined at each point of fluence. The intensity is the amount of radiation per unit cross-sectional area. The magnitude of the fluence may take any of a range of continuous values. However, magnitude of the fluence is typically approximated by discrete fluence levels, i.e. the continuous fluence values are mapped to a set of discrete values.

The fluence is distinct from dose which is the total radiation received by a part of the treatment volume. The dose is a three-dimensional distribution whose magnitude varies as a function of the position within the treatment volume. This variation may be undesirable. In the prior art, improved control over the three-dimensional dose distribution inside the treatment volume may be achieved by rotating the aperture around the treatment volume more than one time. The intensity and spatial distribution of radiation provided by a beam source is changed between consecutive rotations. This may be accomplished, for example, by changing the shape of an aperture within the beam source. The availability of more than one fluence per position along the trajectory of the rotation allows for improved control over the dose distribution. However, this approach results in a variety of disadvantages, for example, rotation of the aperture more than once around the treatment volume requires additional time.

When the radiation source and aperture are rotated around a treatment volume, the projection of the treatment volume onto the aperture may change. As such, it is desirable to change the opening within the aperture as the aperture is moved though different angles. These changes are typically achieved by moving leaves within the aperture to positions determined prior to the treatment. There are several ways in which leaf positions may be determined. In one approach, the projection of the treatment volume along the axis of the radiation beam is determined at each position along the arc of rotation. Two points along the arc of rotation approximately 180 degrees apart will have essentially the same projections (e.g., a mirror image thereof) and, therefore, essentially the same relative leaf configurations. Radiation generated by a beam source is typically constant as the aperture is rotated around the treatment volume. The amount of radiation received by various parts of the treatment volume is, therefore, primarily controlled by the aperture.

One approach to determining leaf positions that can include consideration of the dose received by each part of the treatment volume includes selecting a particular set of leaf positions, for example, by using projections of the treatment volume. The dose distribution throughout the treatment volume is then calculated. After this calculation, the selected set of leaf positions is changed slightly and the projected dose distribution is again calculated. If the change in leaf positions results in an improvement in the dose, the changed leaf positions are kept and the process is repeated. This iterative process may be facilitated by statistical or optimization algorithms. Disadvantages with this approach include lengthy computation times.

SUMMARY

Various embodiments of the invention include systems and methods of managing the positions of aperture leafs so as to improve the radiation treatment of patients. In some embodiments, these systems and methods allow for improved control over the dose received in the treatment volume. In some embodiments, these systems and methods allow for the selection and use of several different discrete fluence levels in a single treatment. For example, leaves may be controlled such that a first part of the treatment volume receives a first amount of radiation and a second part of the treatment volume receives half of the first amount. These parts of the treatment volume and/or the dosage they receive can be designated by a user.

In some embodiments, different leaf configurations are used at opposing points around an arc of rotation to effectively deliver more than one discrete fluence level. For example, in a first position the leaves may be configured to deliver radiation to a first subset of the treatment volume and in a second position, 180 degrees from the first position, the leaves may be configured to deliver the radiation to a second subset of the treatment volume. Those parts of the treatment volume that are included in both the first subset and the second subset receive twice the radiation dose relative to those parts that are included in only one of the first subset and the second subset.

In some embodiments, more than one radiation fluence level is provided by dividing aperture leaves into two or more groups, configuring a first of the two or more groups to provide radiation to a first subset of the treatment volume and configuring a second of the two or more groups to provide the radiation to a second subset of the treatment volume. Those parts of the treatment volume that are included in both the first subset and the second subset receive twice the radiation dose relative to those parts that are included in only one of the first subset and the second subset. Thus, more than one fluence level can be provided at the same time.

The approaches for producing multiple discrete fluence levels per position along the arc of rotation can be used in combination. For example, four discrete fluence levels can be generated by both using different leaf configurations at opposing arc points and by dividing aperture leafs into two or more groups.

Various embodiments of the invention include a radiation treatment system comprising a beam source configured to generate a beam of radiation, a beam aperture including a plurality of aperture leaves configured to shape the beam of radiation, a gantry configured to move the beam aperture, and a computing device configured to control the plurality of aperture leaves so as to provide a dose distribution within a treatment volume while moving the beam aperture 360 degrees or less around the treatment volume using the gantry.

Various embodiments of the invention include a method of determining a configuration of a radiation treatment system, the method comprising receiving a plurality of optimal fluences to be delivered to the treatment volume, the optimal fluences being configured to provide a dose distribution within the treatment volume, determining a plurality of discrete fluence levels to be delivered to the treatment volume, the plurality of discrete fluence levels being determined so as to approximate the optimal fluences, and calculating leaf positions for each leaf of a beam aperture at each of a plurality of beam aperture positions in order to achieve the plurality of discrete fluence levels by moving the beam aperture one or fewer times around an arc of rotation.

Various embodiments of the invention include a computing system comprising a fluence determination engine configured to determine a plurality of radiation fluence levels to produce a desired dose distribution, a leaf position calculator configured to calculate leaf positions for a plurality of leaves in a radiation beam aperture, the leaf positions being configured to provide the plurality of radiation fluence levels to a treatment volume within one rotation of the radiation beam aperture around the treatment volume, and a leaf controller configured to control the plurality of leaves according to the leaf positions calculated using the leaf position calculator.

DETAILED DESCRIPTION

The invention includes systems and methods for providing radiation treatment to a patient. These systems and methods include, for example, a beam source configured to provide a beam of therapeutic radiation. The beam of radiation is shaped by an aperture that is moved, e.g., rotated, around a treatment volume using a gantry. The treatment volume may include a tumor or other part of a patient that benefits from the therapeutic radiation. Some embodiments further include a computing device configured to determine optimum positions for leaves within the aperture. These optimum positions may be configured to provide more than one discrete fluence level during one (or fewer) complete rotation of the aperture around the gantry. Various embodiments of the invention include alternative approaches to providing multiple discrete fluence levels. As is further described herein, some of these approaches may be used in combination.

Figure 1:
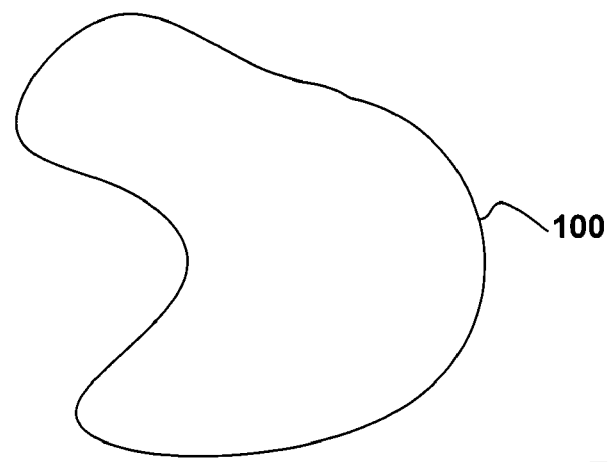
FIG. 1 illustrates a cross-section of an exemplary treatment volume.

FIG. 1 illustrates a cross-section of an exemplary Treatment Volume 100. This cross-section may be projected to an aperture along the direction of a radiation beam. As the position of the aperture changes, the projection of the projected cross-section is also likely to change according to the three-dimensional shape of Treatment Volume 100. In some embodiments, Treatment Volume 100 includes more than one separate volume. For example, Treatment Volume 100 may include two separate tumors separated by healthy tissue. In some embodiments, the treatment volume surrounds a volume of healthy tissue. For example, Treatment Volume 100 may include a tumor that has grown around a healthy tissue. The shape of Treatment Volume 100 shown in FIG. 1 is an arbitrary shape used for illustrative purposes. Treatment Volume 100 may take a wide variety of shapes and, thus, result in a wide variety of cross-sections.

Figure 2:
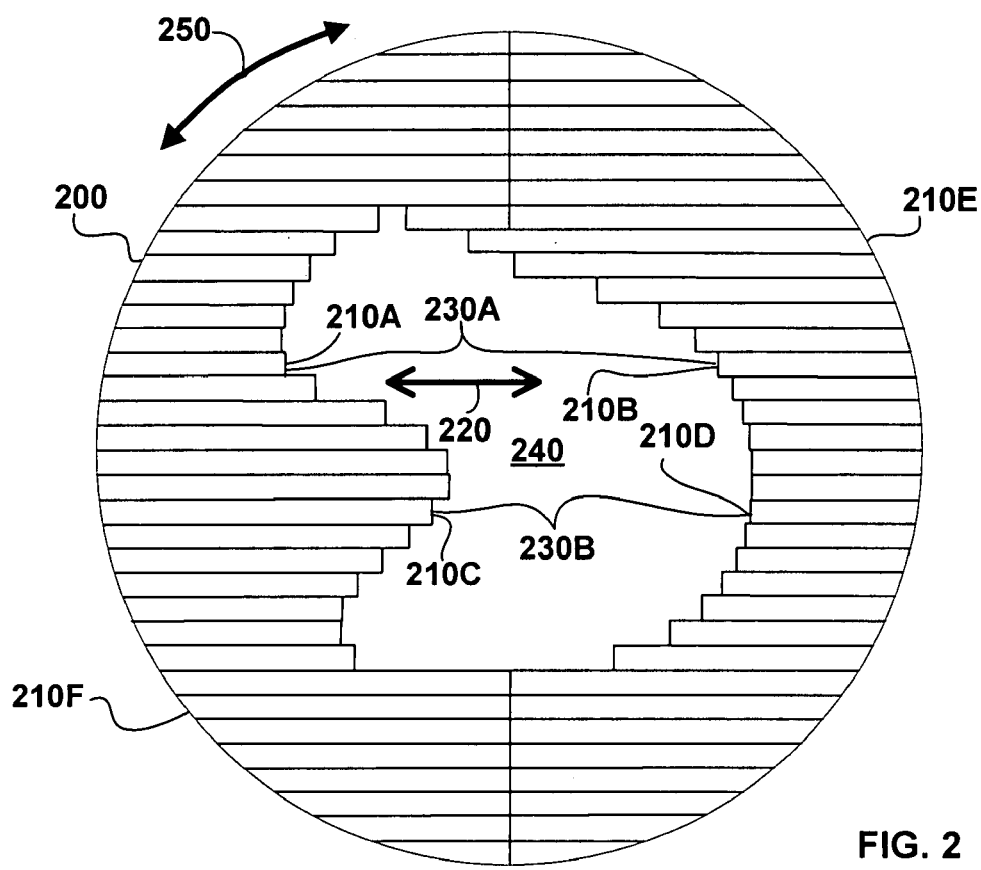
FIG. 2 illustrates an aperture configured to shape a radiation beam to match the treatment volume illustrated in FIG. 1, according to various embodiments of the invention.

FIG. 2 illustrates an Aperture 200 configured to shape a radiation beam to match Treatment Volume 100 illustrated in FIG. 1, according to various embodiments of the invention. Aperture 200 includes a plurality of movable Leaves 210, some of which are individually designated 210A-210F. Each of Leaves 210 typically includes a plate having a thickness in the direction parallel to the radiation beam (perpendicular to the image of FIG. 2) that is sufficient to greatly attenuate that part of the radiation beam that is blocked by one of Leaves 210. Opposing members of Leaves 210 are referred to as Leaf Pairs 230. For example, Leaves 210A and 210B comprise a Leaf Pair 230A. Likewise, Leaves 210C and 210D comprise a Leaf Pair 230B.

Leaves 210 may be moved in Directions 220 in order to provide one or more Opening 240. For example, in FIG. 2

Leaf Pair 230A is disposed to match the projection of Treatment Volume 100 along the direction of the radiation beam to Aperture 200. Opening 240 may include a single opening as illustrated in FIG. 2, or a plurality of separate openings as illustrated elsewhere herein. In some embodiments, Aperture 200 can be rotated within the plane of the figure, e.g., in Directions 250.

Figure 3:
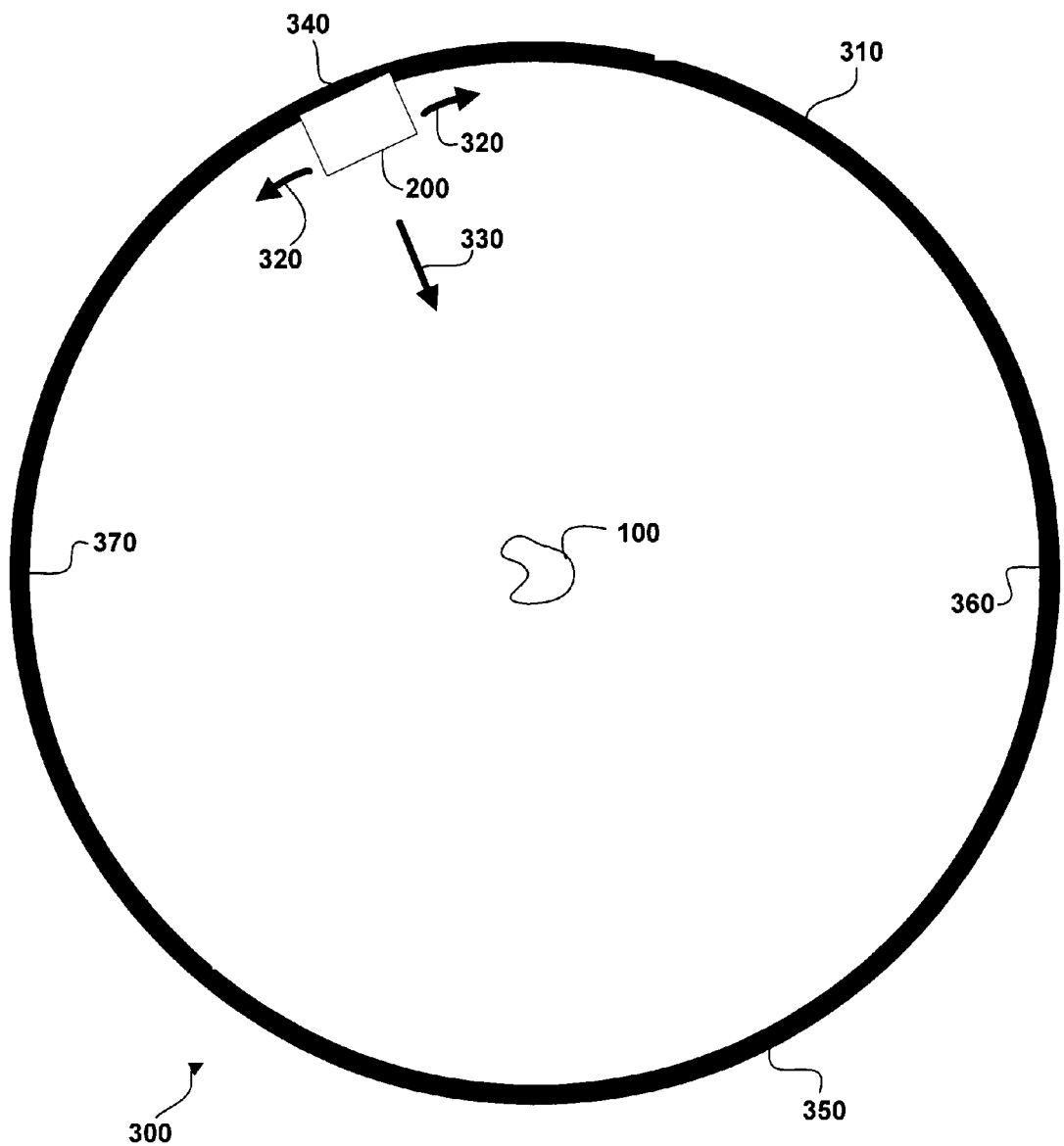
FIG. 3 illustrates a radiation treatment system including a 360 degree gantry configured to support and move the aperture of FIG. 2, according to various embodiments of the invention.

FIG. 3 illustrates a Radiation Treatment System, generally designated 300 and including a 360 degree Gantry 310 configured to support and move Aperture 200 of FIG. 2. Gantry 310 is configured to move Aperture 200 and optionally part of a beam source (not shown) in directions 320. As Aperture 200 is moved around Treatment Volume 100, the beam of radiation travels from Aperture 200 to Treatment Volume 100 from a variety of directions. For example, at the position of Aperture 200 illustrated in FIG. 3, a radiation beam is directed in a Direction 330.

As Aperture 200 is moved around Treatment Volume 100, the projection of Treatment Volume 100 onto Aperture 200 changes according to the three-dimensional shape of the Treatment Volume 100. As is further described herein, this changing projection is one of the factors that may be used to determine a position for leaves 210. The projection of Treatment Volume 100 will be approximately the same when Aperture 200 is positioned in opposing positions around Gantry 310. For example, the projections from a Position 340 and a Position 350 will be approximately the same. For the purposes of this discussion, these positions are referred to herein as the 11:00 and 5:00 positions respectively. Likewise, a Position 360 and a Position 370 are referred to herein as the 3:00 and 9:00 positions respectively. Other positions may be referred to herein using similar clock based references.

Figure 4:
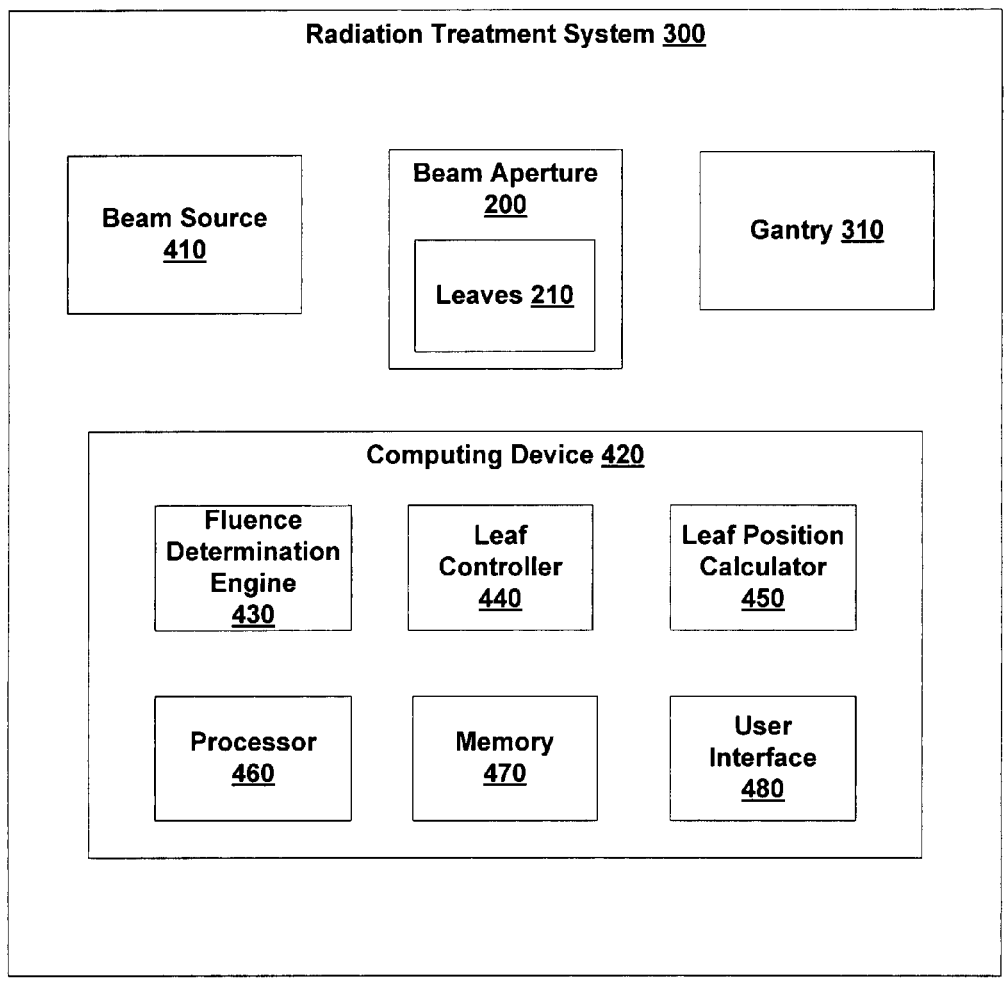
FIG. 4 is a block diagram of a radiation treatment system, according to various embodiments of the invention.

FIG. 4 is a block diagram of Radiation Treatment System 300, which includes a Beam Source 410, Beam Aperture 200 and Gantry 310. Beam Source 410 is configured to generate a beam of therapeutic radiation. This beam of radiation may include x-rays, particles, and/or the like. For example, in some embodiments, Beam Source 410 includes an x-ray source. In some embodiments, Beam Source 410 includes a particle beam source such as a particle accelerator. Beam Source 410 is optionally configured for generating imaging radiation as well as therapeutic radiation.

Radiation Treatment System 300 further includes a Computing Device 420 configured to determine radiation fluence levels using a Fluence Determination Engine 430, to send signals to Beam Aperture 200 to position Leaves 210 using a Leaf Controller 440, and to calculate leaf positions using a Leaf Position Calculator 450.

Computing Device 420 typically further comprises a Processor 460 and Memory 470. Processor 460 is configured to execute computing instructions in order to perform methods and functions described herein. These computing instructions may be embodied in hardware, firmware, and/or software. Memory 470 is configured to store the computing instructions, data related to the three-dimensional dose distribution, data related to fluences, data defining the treatment zone, calculated leaf positions, and/or the like. Computing Device 420 may further include a User Interface 480. User Interface 480 may include a display and/or a graphical user interface, and is configured for a user to control Radiation Treatment System 300, designate fluence levels, designate a treatment volume, and/or the like.

Fluence Determination Engine 430 is configured for determining a plurality of optimal fluences appropriate for achieving a desired three-dimensional dose distribution within a treatment volume. These optimal fluences are optionally continuous rather than discrete. For example, in some embodiments, Fluence Determination Engine 430 is configured to receive specifications for a desired three-dimensional dose distribution from a user via User Interface 480. The spatial characteristics of the desired three-dimensional dose distribution may be designated manually by having the user mark boundaries of the spatial distribution on an image of Treatment Volume 100. Alternatively, the spatial distribution may be automatically designated by applying a filter to an image of Treatment Volume 100. For example, the spatial distribution may be designated by selecting image pixels within a certain intensity range. Designation of the spatial distribution may include both manual and automated approaches. Typically, the spatial distribution is selected to avoid delivering radiation to healthy radiation sensitive organs.

Figure 5A:
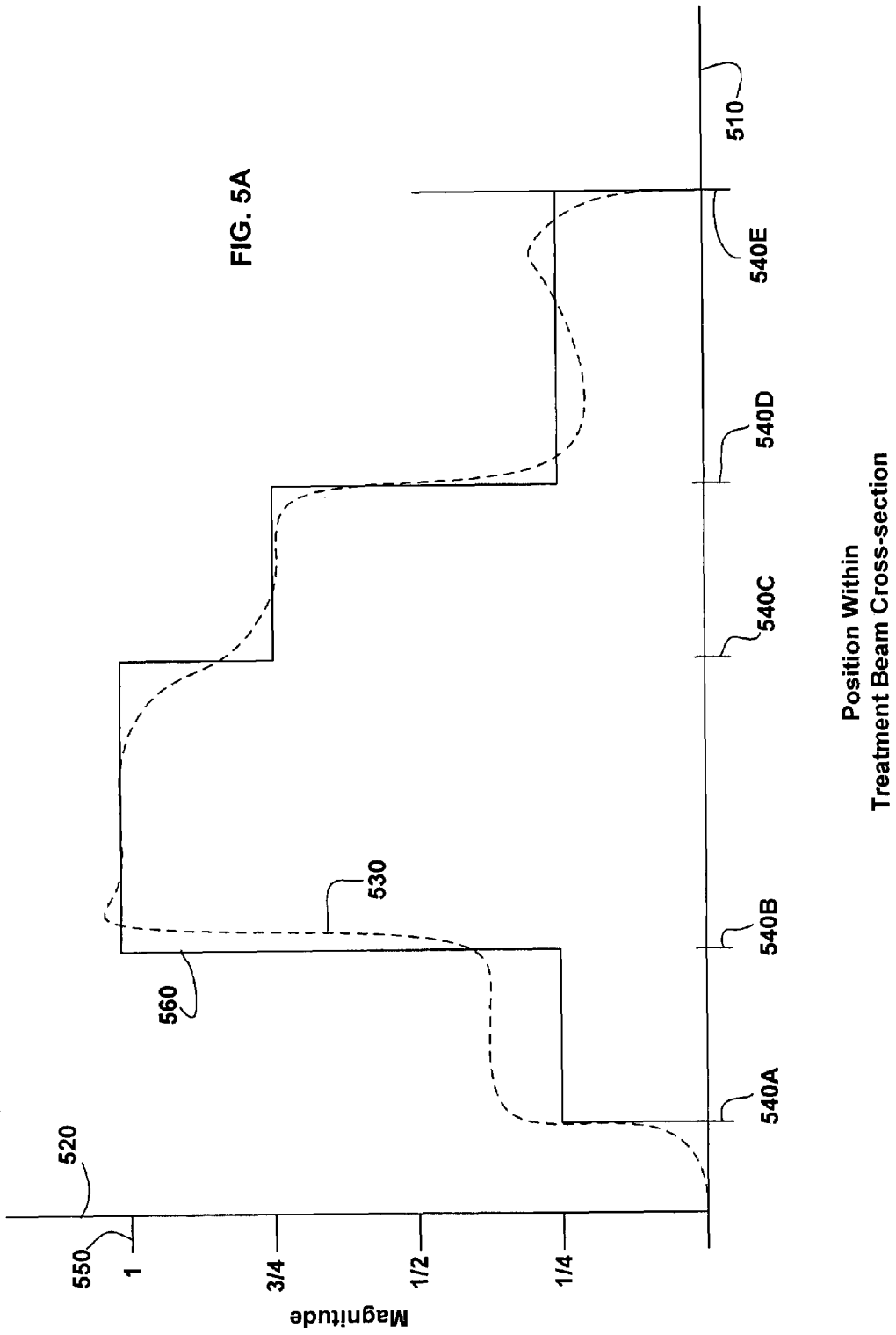
FIG. 5A illustrates a plurality of discrete fluence levels, according to various embodiments of the invention.

FIG. 5A illustrates a plurality of discrete fluence levels (solid line), approximating the optimal fluences (dotted line) as may be appropriate for an exemplary treatment. In FIG. 5A, the X-axis 510 represents position within a cross-section of Aperture 200 and the Y-axis 520 represents a normalized magnitude of the fluence. The magnitude of the optimal fluences is represented by a Dashed Line 530. As shown in FIG. 5A, the magnitude of the fluence varies as a function of position. Between a Position 540A and a Position 540B, and a Position 540D and a Position 540E, the discrete fluence level is approximately ¼ of the Maximum Discrete Fluence 550. Between Position 540B and a Position 540C, the discrete fluence level is approximately equal to the Maximum Discrete Fluence 550. Between Position 540C and the Position 540D, the discrete fluence level is approximately ¾ of the Maximum Discrete Fluence 550. In some embodiments, Fluence Determination Engine 430 is configured to calculate the continuous fluences in order to achieve a desired three-dimensional dose distribution for each point within the Treatment Volume 100.

The optimal fluences are used, by the Fluence Determination Engine 430, to determine the plurality of discrete fluence levels. The discrete fluence levels are typically selected so as to best approximate the optimal fluences. For example, in FIG. 5A, the selected discrete fluence levels are illustrated by Solid Line 560. These discrete fluence levels are selected to approximate the optimal fluences illustrated by Dashed Line 530. Because the optimal fluences may vary as a function of gantry angle, Fluence Determination Engine 430 is optionally configured to select a different set of discrete fluence levels for each gantry angle. The selection of discrete fluence levels may be manual or automatic.

In some embodiments, determined discrete fluence levels from opposing gantry positions are summed or averaged. This can significantly simplify the determination of the discrete fluence levels. Summing or averaging the discrete fluence levels from opposing gantry positions is possible because the projection of Treatment Volume 100 in opposite directions is approximately the same. (These projections are not necessarily exactly the same because the radiation beam typically has some divergence.)

As is described further herein, the discrete fluences levels are sometimes restricted to being simple ratios of each other. For example, the discrete fluence levels may be in ratios of 1:½, 1:¼, 1:¾, 1:⅓, 1:⅔, and/or the like. Further, more than two fluence levels may be selected for use during a single movement around Gantry 310. For example, FIG. 5A illustrates three discrete fluence levels in ratios of 1:¾, 1:¼ and 1:⅓. (The discrete fluence levels in the ratio of 1:⅓ can be found by comparing the fluence between Positions 540C and 540D to the fluence between Positions 540D and 540E.) A greater number of discrete fluence levels can allow for an improved approximation of the optimal fluences. For example, using the three discrete fluence levels illustrated in FIG. 5A, between Positions 540A and 540B the discrete fluence level is substantially below the optimal fluences. A fourth discrete fluence level of approximately ⅜ of the Maximum Discrete Fluence 550 would allow a better approximation in this particular example.

Figure 5B:
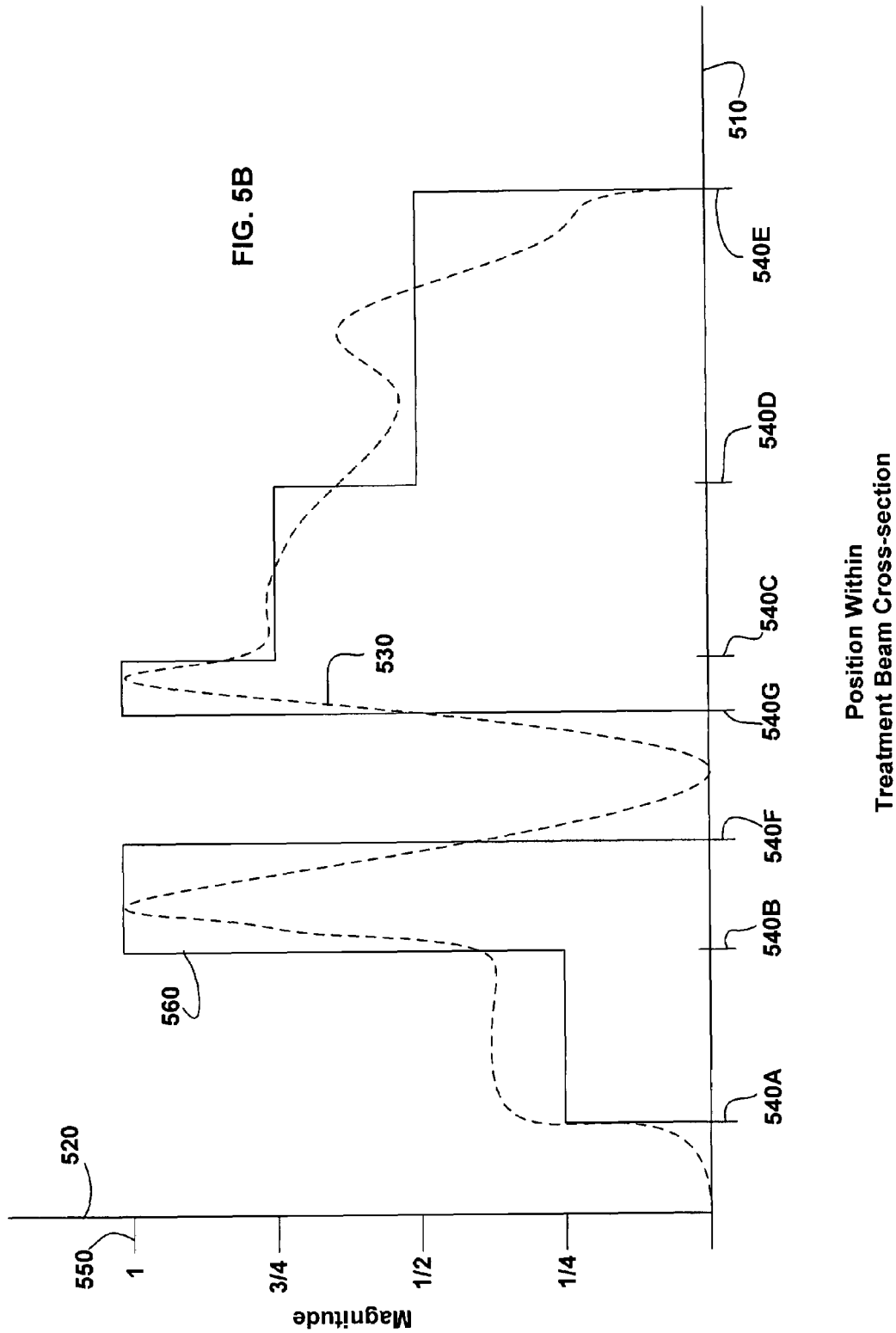
FIG. 5B illustrates an alternative plurality of discrete fluence levels, according to various embodiments of the invention.

FIG. 5B illustrates an alternative shape of the optimal fluences and corresponding discrete fluence levels. These discrete fluence levels include a region, between a Position 540F and a Position 540G, in which the optimal fluences are approximated with a discrete fluence level of zero. Such a distribution may be desirable to protect radiation sensitive organs, e.g. a spinal cord. Typically, a greater the number of discrete fluence levels allows for a better the match between the discrete fluence levels and the optimal fluences.

Referring again to FIG. 4, Leaf Controller 440 is configured to send control signals to Beam Aperture 200 so as to move Leaves 210 to the leaf positions calculated using Leaf Position Calculator 450. In some embodiments, these control signals include digital data to be delivered to Beam Aperture 220. Leaf Controller 440 may include computing instructions and/or hardware configured for communication and signal processing.

Leaf Position Calculator 450 is configured to calculate positions for each Leaf 210 at each position of Gantry 310. These leaf positions are calculated so as to achieve the discrete fluence levels selected using Fluence Determination Engine 430. Typically, Leaf Position Calculator 450 starts the calculation of leaf positions by a) assigning Leaves 210 to different groups, and/or b) by assigning different positions of Aperture 200 (relative to Gantry 310) to different groups. Thus, groups may include sets of Leaves 210 and/or sets of positions of Aperture 200. In some embodiments, Leaves 210 are assigned on the basis of Leaf Pairs 230. For example, each opposing Leaf Pair 230 may be assigned together to a group. Each group is configured to provide radiation to a different volume within Treatment Volume 100. Further details of these assignments are discussed elsewhere herein.

Figure 6A:
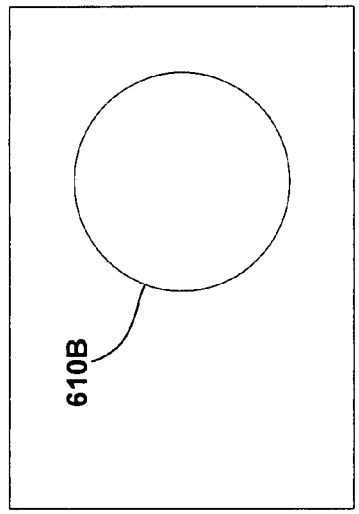
FIGS. 6A-6D are illustrations of how different groups can be used to provide a plurality of discrete fluence levels, according to various embodiments of the invention.
Figure 6B:
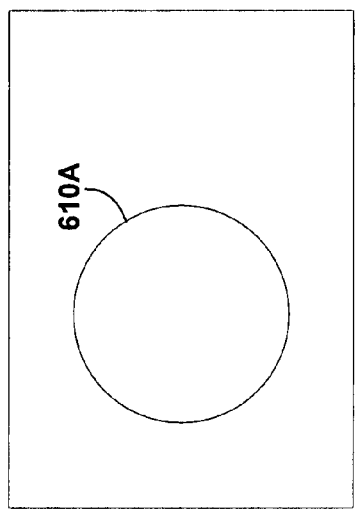

FIGS. 6A-6D are an illustration of how different groups (of Leaves 210 and/or positions) can be used to provide a plurality of discrete fluence levels. FIG. 6A shows an Area 610A that will be radiated using a first group and FIG. 6B shows an Area 610B to be radiated using a second group. These areas are in a plane through Treatment Volume 100 and perpendicular to the direction of the radiation beam. For example, in the example illustrated in FIG. 3, if the Aperture were in the 11:00 Position 340, the plane through Treatment Volume 100 would be perpendicular to the Direction 330. During a single movement of Aperture 200 around Gantry 310 the radiation generated using Beam Source 410 is approximately constant, as such, each of Area 610A and 610B receive the same fluence of radiation. For the purposes of illustration, this fluence can be referred to as fluence "X."

Figure 6C:
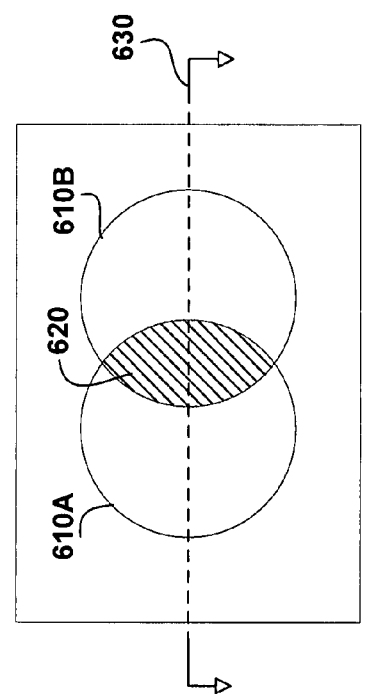

FIG. 6C shows the combined effects of radiation received by the Treatment Volume 100 due to both the first group and the second group. Some parts of Treatment Volume 100 receive radiation only as a result of the first group, some parts of Treatment Volume 100 receive radiation only as a result of the second group, and some parts of the Treatment Volume 100 (illustrated by Hash Marks 620) receive radiation as a result of both the first group and the second group. Those parts of Treatment Volume 100 that receive radiation only as a result of one group receive a fluence of level "X," while those parts of Treatment Volume 100 that receive radiation as a result of both groups receive a fluence of level "2X." As such, two different discrete fluence levels are achieved in a ratio of 1:½. More than two groups may be used to achieve more than two discrete fluence levels. For example, in some embodiments, two groups are established by assignment of Leaf Pairs 230 and two groups are established by assignment of positions of Aperture 200. These two groups may be used to achieve two, three or four discrete fluence levels.

Figure 6D:
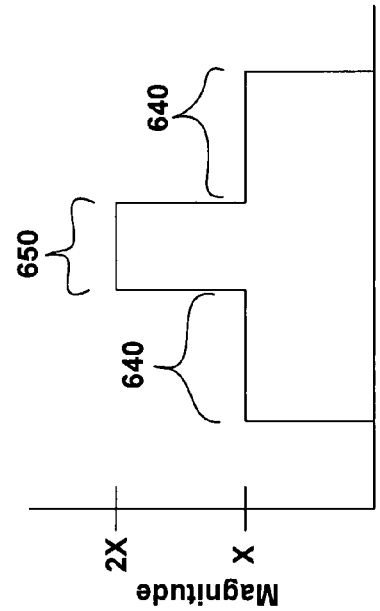

FIG. 6D illustrates the discrete fluence levels resulting from the groups illustrated in FIG. 6C along a Cross-section 630. As shown, in some Positions 640 a fluence of "X" is achieved while in other Positions 650 a fluence of "2X" is achieved. More than two groups may be used to achieve more than two discrete fluence levels.

Figure 7A:
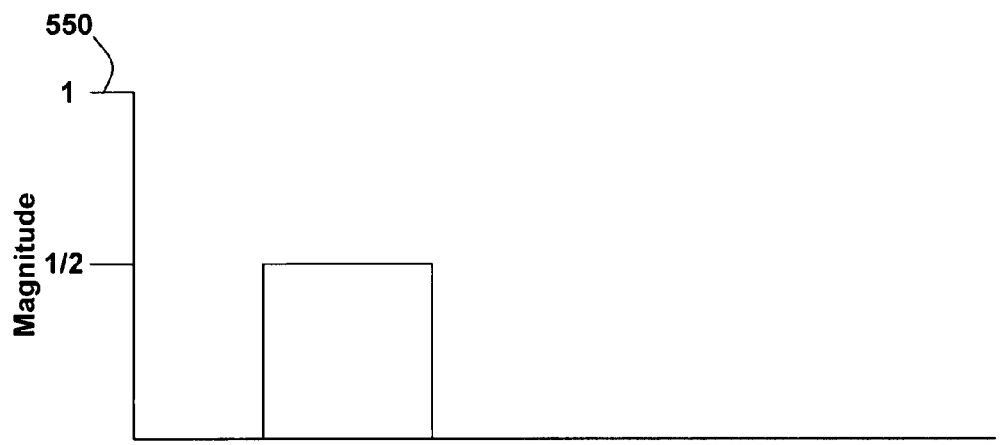
FIGS. 7A-7F illustrate further examples of how different groups is can be used to generate discrete fluence levels, according to various embodiments of the invention.
Figure 7B:
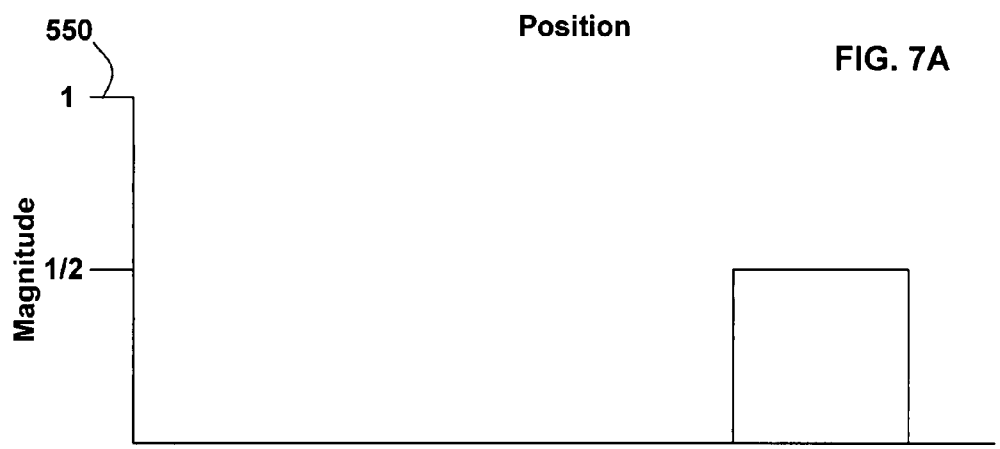
Figure 7C:
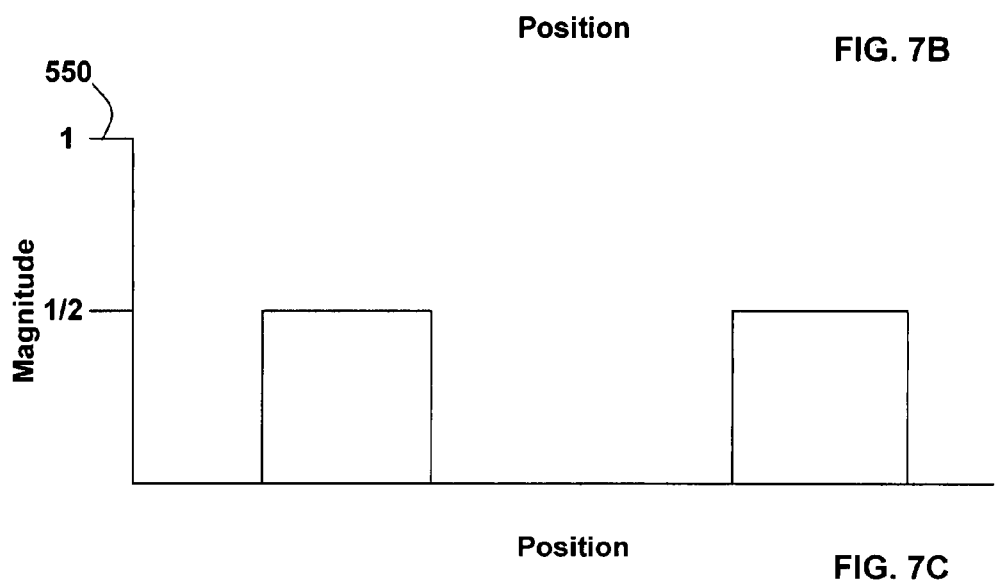
Figure 7D:
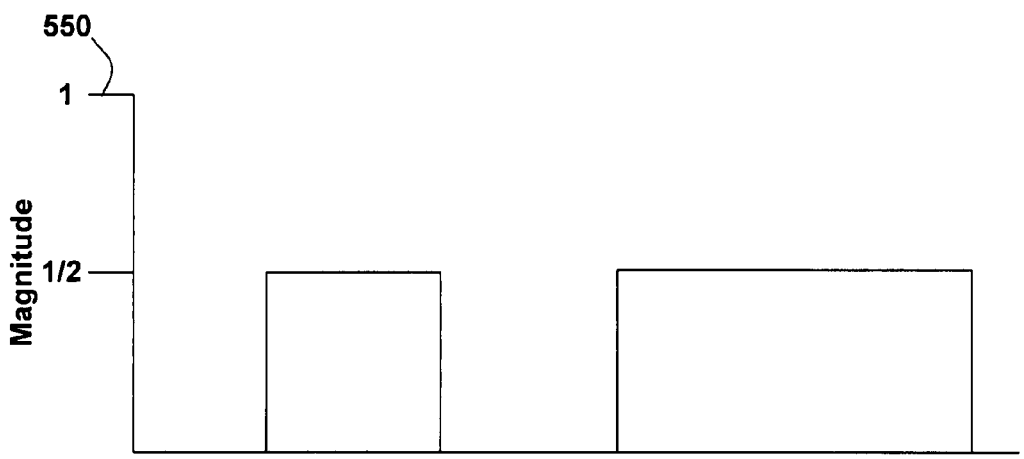
Figure 7E:
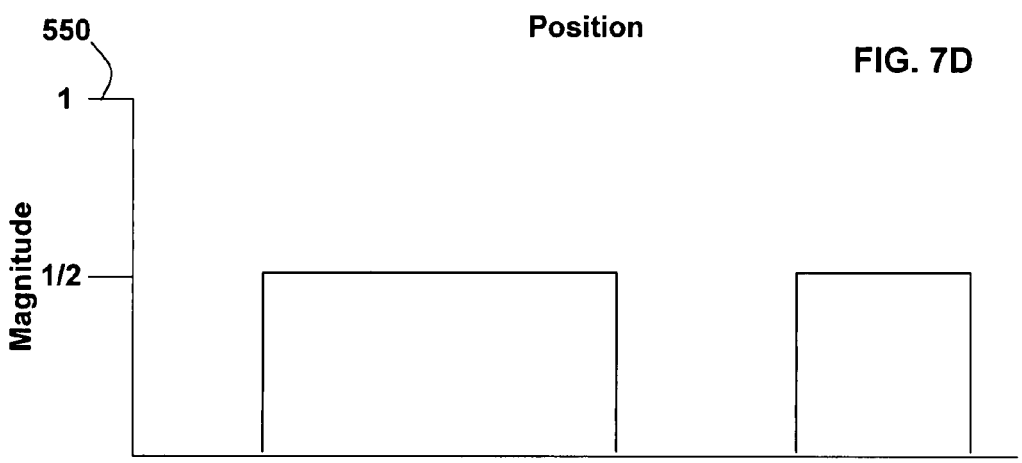
Figure 7F:
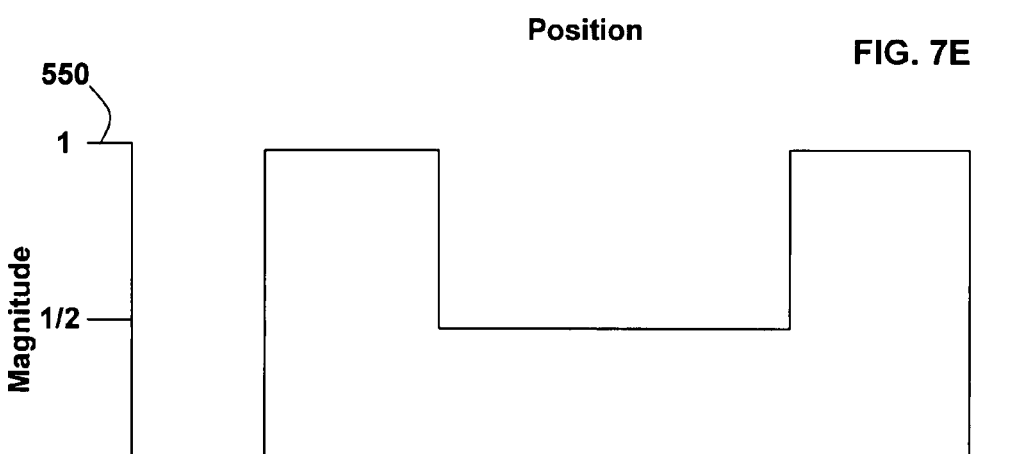

FIGS. 7A-7F illustrate further examples of how different groupings can be used to generate multiple discrete fluence levels. FIGS. 7A and 7B illustrate fluence magnitude as a function of position along a cross-section such as Cross-section 630. FIG. 7A illustrates the fluence resulting from a first group while FIG. 7B illustrates the fluence resulting from a second group. FIG. 7C illustrates the combined fluence that can be achieved using the first and second group in a single movement of Beam Aperture 200 around Gantry 310. Likewise, FIGS. 7D and 7E illustrate fluences resulting from a third group and a fourth group, respectively. More than one leaf pair assigned to separate groups are required to generate a fluence including a gap such as that illustrated in FIGS. 7D and 7E. FIG. 7F illustrates the combined fluence that can be achieved using the third and fourth groups in a single movement (rotation) of Beam Aperture 200 around Gantry 310.

In some embodiments, Leaf Position Calculator 450 is configured to assign different positions of Aperture 200 around Gantry 310 to different groups each configured to provide radiation to a different part, e.g. subset, of Treatment Volume 100. For example, the 11:00 o'clock Position 340 may be assigned to a first group and the 5:00 o'clock Position 350 may be assigned to a second group. As a result of these assignments, at the 11:00 o'clock Position 340, as shown in FIG. 3, Leaf Pairs 230 will be configured to deliver radiation to a first part of Treatment Volume 100, and at the 5:00 o'clock Position 350 Leaf Pairs 230 will be configured to deliver radiation to a second part of Treatment Volume 100. As illustrated in FIGS. 6A-6D and 7A-7F, these parts of Treatment Volume 100 may overlap to achieve multiple discrete fluence levels. This approach is different than the prior art wherein relative leaf positions at opposing points around Gantry 310 are typically the mirror image of each other so as to radiate the same part of a treatment volume. Each pair of opposing positions around Gantry 310 is optionally assigned to the first group and the second group in a similar manner. In one embodiment, the positions 12:00 clockwise to 5:59 are assigned to the first group and the positions 6:00 clockwise to 11:59 are assigned to the second group. When different groups are assigned to different positions around Gantry 310, multiple discrete fluence levels can be achieved without substantial degradation of the spatial resolution to which radiation is delivered to Treatment Volume 100.

In some embodiments, Leaf Position Calculator 450 is configured to assign different Leaves 210 and/or Leaf Pairs 230 to different groups. For example, every second, third or fourth member of Leaf Pairs 230 may be assigned to a different group. Using this approach, the first, third, fifth, etc., Leaf Pairs 230 may be assigned to a first group and the second, fourth, sixth, etc., Leaf Pairs 230 may be assigned to a second group. The assignment of different Leaf Pairs 230 may be done in combination with assignment of different positions of Aperture 200 to different groups. This combination can result in three or four different groups and, thus, up to four different discrete fluence levels.

Figure 8:
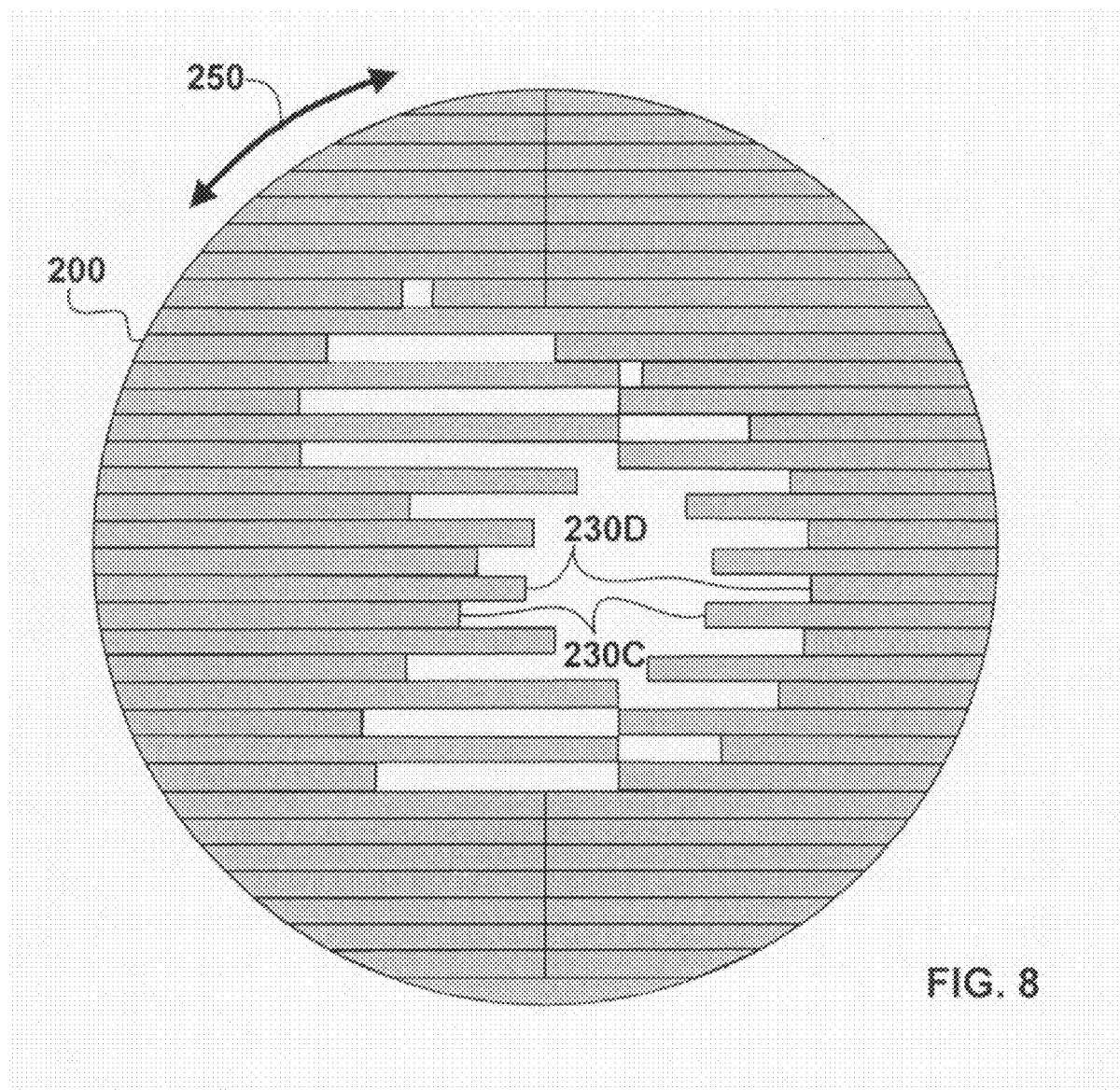
FIG. 8 illustrates an example of an aperture wherein leaf pairs are divided into two groups by assigning alternating member of the leaf pairs to a different group, according to various embodiments of the invention.
Figure 9A:
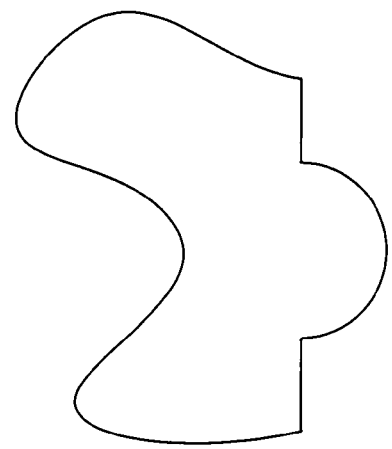
FIG. 9A illustrates a part of a treatment volume that would be radiated by the first group of FIG. 8, according to various embodiments of the invention.
Figure 9B:
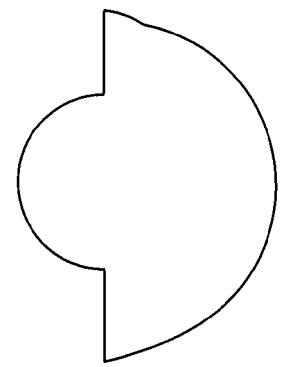
FIG. 9B illustrate the part of a treatment volume that would be radiated by the second group of FIG. 8, according to various embodiments of the invention.
Figure 9C:
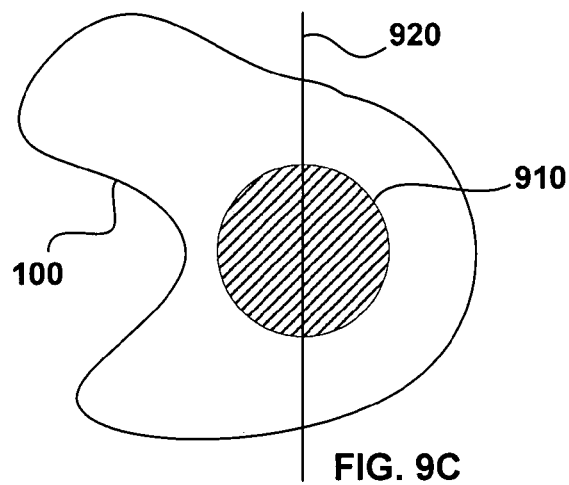
FIG. 9C illustrates the combined fluence levels achieved using the first group and the second group of FIG. 8, according to various embodiments of the invention.
Figure 9D:
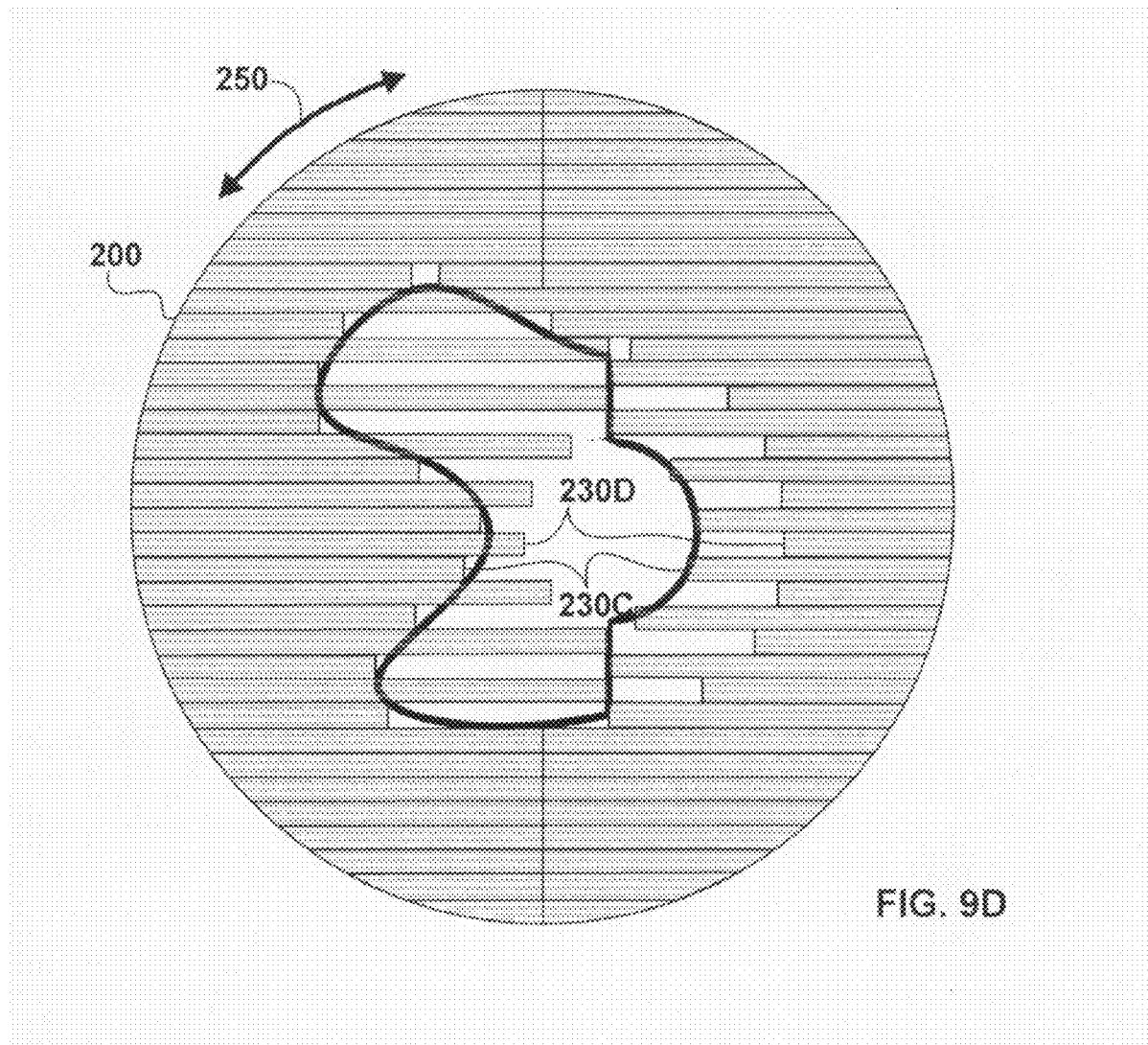
FIG. 9D illustrates an overlay of FIG. 8 on FIG. 9A.
Figure 9E:
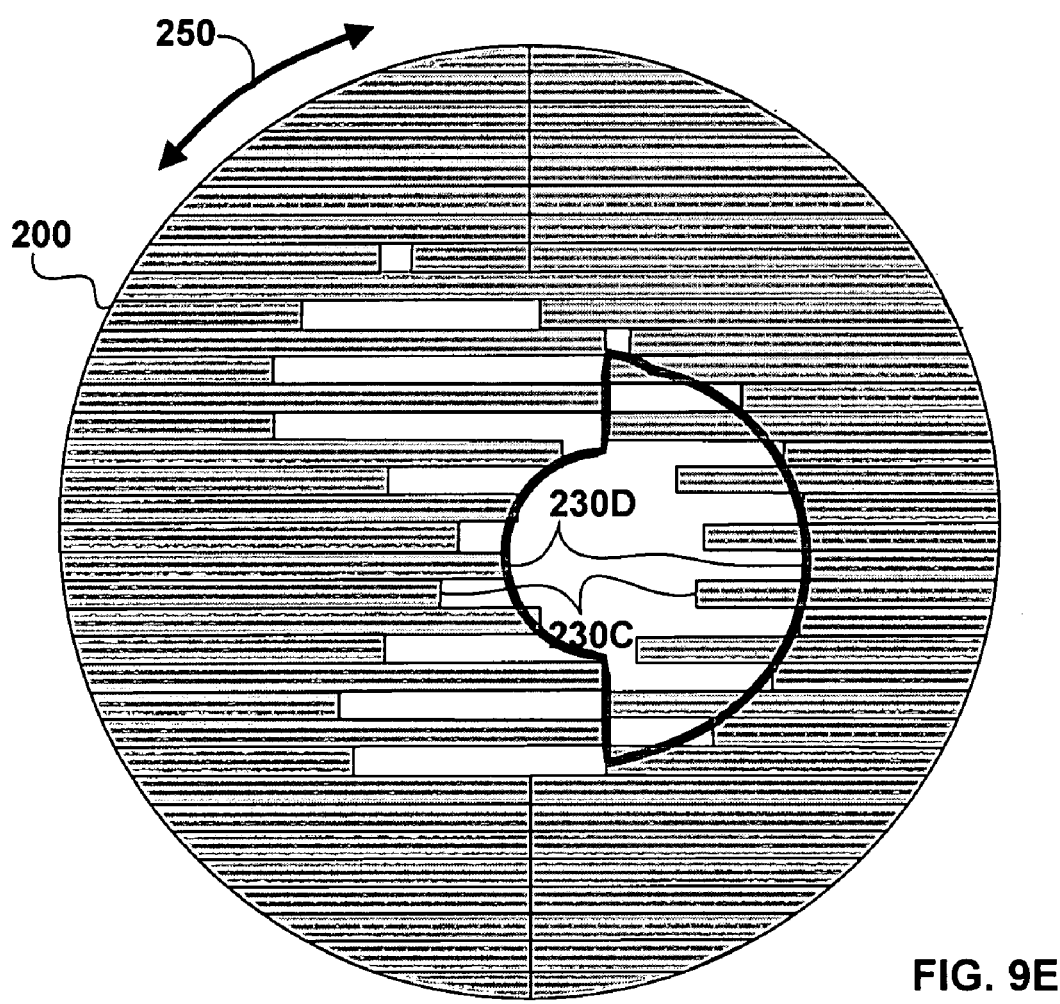
FIG. 9E illustrates an overlay of FIG. 8 on FIG. 9B.

FIG. 8 illustrates an example of Aperture 200 wherein Leaves 210 are divided into two groups by assigning alternating member of Leaf Pairs 230 to a different group. For example, Leaf Pair 230C is assigned to a first group and Leaf Pair 230D is assigned to a second group. Each if these groups is configured to apply radiation to a different part of Treatment Volume 100. FIG. 9A illustrates the part of Treatment Volume 100 that would be radiated by the first group and FIG. 9B illustrate the part of Treatment Volume 100 that would be radiated by the second group. The magnitude of the radiation fluence across the parts of Treatment Volume 100 illustrated in FIGS. 9A and 9B may vary somewhat due to the reduction in spatial resolution that results from the use of alternating Leaf Pair 230 to control the distribution of radiation in each group. However, approaches to reducing this variation are discussed elsewhere herein. FIG. 9C illustrates the combined discrete fluence levels achieved using the first group and the second group. A Region 910 receives a discrete fluence level twice that of other parts of Treatment Volume 100 because Region 910 is included in both the first group and the second group.

In practice, Aperture 200 may include more or fewer Leaf Pairs 230 than shown in FIGS. 2 and 8. A greater number of Leaf Pairs 230 per unit area will result in a higher resolution in the distribution of radiation within Treatment Volume 100. Thus, the effects of using alternating Leaf Pair 230 to define parts of Treatment Volume 100 may partially be compensated for by including a greater number of Leaf Pairs 230 in Beam Aperture 200. Further, the examples illustrated by FIGS. 8 and 9A-9C correspond to one projection of Treatment Volume 100 to one position of Beam Aperture 200 around Gantry 310. The projection of Treatment Volume 100 may be different at different positions around Gantry 310 and the parts of Treatment Volume 100 to which Leaf Pairs 230 in the first group and the second group are configured to provide radiation are typically three-dimensional volumes. As such, the relative positions of Leaf Pairs 230 within Gantry 310 may change as Beam Aperture 200 is moved around Gantry 310. These changes may partially compensate for the effects of using alternating Leaf Pair 230 to radiate a part of Treatment Volume 100.

In some embodiments, Beam Aperture 200 is configured to rotate in Directions 250 as indicated in FIG. 2, e.g. around the direction of propagation of the radiation. This rotation may occur while Beam Aperture 200 is stopped at one or more positions around Gantry 310 and/or may occur as Beam Aperture 200 is moved around Gantry 310. Because rotation of Beam Aperture 200 in Directions 250 changes which particular members of Leaf Pairs 230 cover particular parts of Treatment Volume 100, rotation of Beam Aperture 200 may reduce the resolution related effects of using alternating Leaf Pair 230 to radiate parts of Treatment Volume 100.

Leaf Position Calculator 450 may further be configured for determining how to divide Treatment Volume 100 into different parts for treatment using different groups of Leaf Pairs 230. In some embodiments, each projection of Treatment Volume 100 is divided using an arbitrary division line. On one side of the division line those parts of Treatment Volume 100 that are to receive the lowest discrete fluence level are assigned to a first group, and on the other side of the division line those parts of Treatment Volume 100 that are to receive the lowest discrete fluence level are assigned to a second group.

For example, a Division Line 920 is shown intersecting Treatment Volume 100 in FIG. 9C. Those parts of Treatment Volume 100 that are to receive the lowest discrete fluence level and are to the left of Division Line 920 are assigned to the first group. Those parts that are to receive the lowest discrete fluence level and are to the right of Division Line 920 are assigned to the second group. Those parts of Treatment Volume 100 that are to receive a greater discrete fluence level are assigned to both the first group and the second group. The resulting radiation distributions are illustrated in FIGS. 9A and 9B, respectively.

To clarify the relationship between the radiation distributions illustrated in FIGS. 9A and 9B, FIGS. 9D and 9E illustrate overlays of FIG. 8 on FIGS. 9A and 9B, respectively.

Figure 10A:
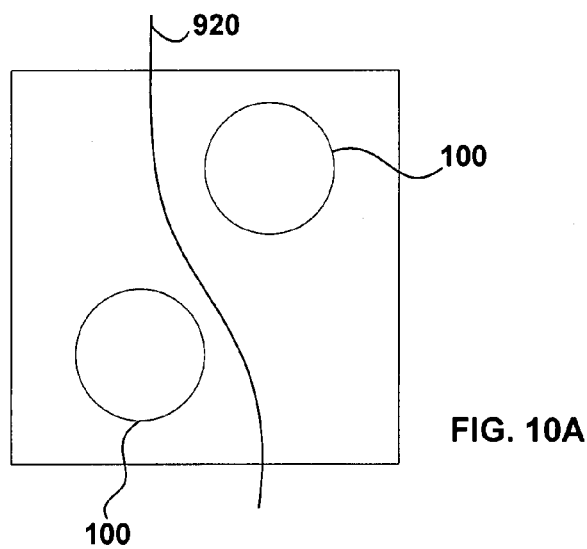
FIGS. 10A and 10B illustrate various ways a treatment volume can be divided using a division line.
Figure 10B:
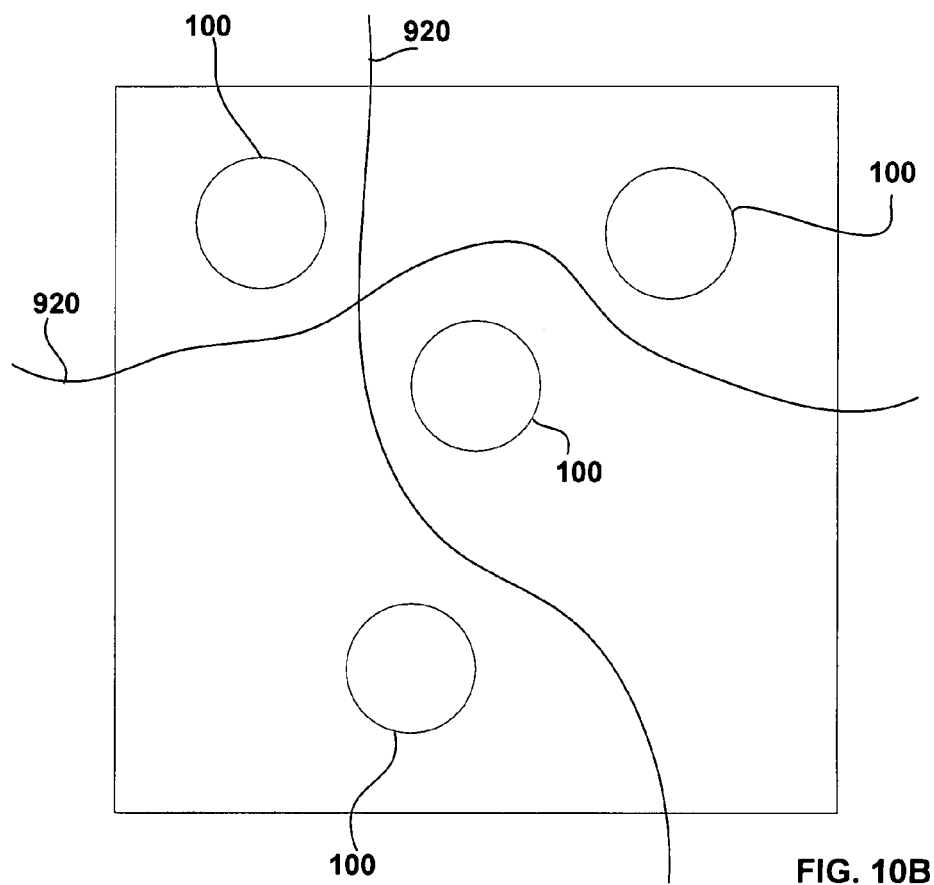

Division Line 920 need not be a straight line. For example, FIG. 10A illustrates the use of a curved Division Line 920 to separate disjoint parts of Treatment Volume 100. The separate disjoint parts of Treatment Volume 100 are radiated by using Aperture Leaves 210 to create at least two separate openings in the same aperture at the same time. Further, Treatment Volume 100 may be divided using a plurality of alternative Division Lines 920. FIG. 10B illustrates two alternative Division Lines 920 that may be used to separate parts of Treatment Volume 100. In some embodiments, Division Line 920 changes as Beam Aperture 200 moves around Gantry 310. Several division lines can be used simultaneously. Further, any two dimensional region within a target can be assigned to a group of leaf pairs.

In some embodiments, each of Division Line 920 is automatically generated using Leaf Position Calculator 450. In some embodiments, Division Line 920 is manually selected by a user using User Interface 480. For example, a user may use User Interface 480 to manually draw Division Line 920 on an image of Treatment Volume 100.

In some embodiments, Leaf Position Calculator 450 is configured to calculate positions for each Leaf Pair 230 at each position around Gantry 310. These calculations may include consideration of the mechanical limitations of Beam Aperture 200. For example, the speed at which Leaves 210 can be moved may be limited and it may be undesirable to have to wait for leaf movement as Beam Aperture 200 is moved around Gantry 310. Calculated positions for each Leaf Pair 230 may, therefore, be automatically reviewed to assure that they can be efficiently implemented using Beam Aperture 200. If moving each Leaf Pair 230 to the calculated positions would significantly slow the treatment process, then Leaf Position Calculator 450 may automatically modify the calculated positions, or perform new calculations of leaf positions using different Division Lines 920 and/or rotational orientations of Beam Aperture 200.

Figure 11:
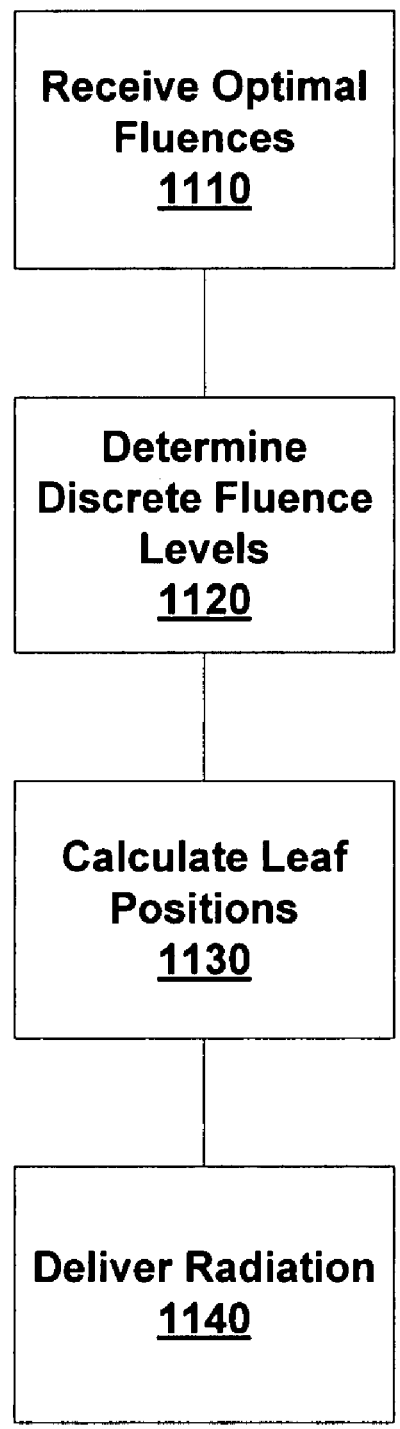
FIG. 11 methods of providing radiation to a treatment volume, according to various embodiment of the invention.

FIG. 11 illustrates methods of providing radiation to a treatment volume, such as Treatment Volume 100, according to various embodiment of the invention. In these methods, a plurality of optimal fluences is calculated, a plurality of discrete fluence levels is selected in order to approximate the optimal fluences, leaf positions are calculated, and the calculated leaf positions are optionally used to deliver radiation to a treatment volume.

In a Receive Optimal Fluences Step 1110, a plurality of optimal fluences to be delivered to Treatment Volume 100 is received. These optimal fluences are optionally continuous and have been determined in order to achieve the desired three-dimensional dose distribution in the treatment volume. The characteristics of the desired three-dimensional dose distribution have been specified by a user, e.g., by a medical doctor, by a physicist or by a dosimetrist, based on medical needs. The user may specify that the values of the three-dimensional dose distribution need to be lower, or smaller, near radiation sensitive healthy tissue. The values of the desired three-dimensional dose distribution will typically vary as a function of position within the Treatment Volume 100. The Fluence Determination Engine 430 used the three-dimensional dose distribution to calculate the two-dimensional optimal fluences for each static Gantry 310 angle.

In a Determine Discrete Fluence Levels Step 1120, a plurality of discrete fluences levels is selected to approximately reproduce the, optionally continuous, optimal fluences, received in Receive Optimal Fluences Step 1110. The selected discrete fluence levels may be similar to those illustrated by Solid Line 560 in FIGS. 5A and 5B. In some embodiments, Determine Fluence Levels Step 1120 is performed automatically using Fluence Determination Engine 430. In these embodiments, Processor 460 is used to calculate two, three, four, or more discrete fluence levels. In some embodiments, Determine Fluence Levels Step 1120 is performed with input from a user using User Interface 480. For example, a user may adjust the discrete fluence levels determined using Fluence Determination Engine 430, or the user may determine the discrete fluence levels manually.

In a Calculate Leaf Positions Step 1130, positions of Leaves 210 and/or Leaf Pairs 230 at each of a plurality of beam aperture positions are calculated. These positions of Leaf Pairs 230 are calculated to achieve the plurality of discrete fluence levels by moving the beam aperture one or fewer times around an arc of rotation, such as that characterized by Gantry 310. For example, in some embodiments the leaf positions are calculated to achieve the plurality of discrete fluence levels by moving the beam aperture once around Gantry 310. In some embodiments, the leaf positions are calculated to achieve the plurality of discrete fluence levels by moving the beam aperture part of the way around Gantry 310, e.g., from the 12:00 position clockwise to the 11:00 position. Calculate Leaf Positions Step 1130 optionally includes calculation of how to rotate Aperture 200 in Directions 250 as illustrated in FIG. 2.

Calculate Leaf Positions Step 1130 optionally includes associating a first part of Leaves 210 with a first discrete fluence level in the beam aperture positions around Gantry 310 and associating a second part of Leaves 210 with a second discrete fluence level in the beam aperture positions. When the first group and the second group are related to aperture positions, individual Leaf Pairs 230 are configured to deliver radiation to the first part of Treatment Volume 100 at gantry positions associated with the first group and configured to deliver radiation to the second part of the treatment volume at gantry positions associated with the second group. In some embodiments, opposing gantry positions are associated with different groups.

Calculate Leaf Positions Step 1130 optionally includes assigning a first Leaf Pair 230 of Beam Aperture 200 to a first group and assigning a second Leaf Pair 230 of Beam Aperture 200 to a second group. The first Leaf Pair 230 is configured to deliver radiation to the first part of Treatment Volume 100 and the second leaf pair is configured to deliver radiation to the second part of Treatment Volume 100. For example, in some embodiments, alternating Leaf Pairs 230 may be assigned to the first group and second group respectively. In some embodiments, every third or every fourth Leaf Pair 230 is assigned to the same group and other Leaf Pairs 230 are assigned to other groups. Radiation is optionally delivered to both the first part and second part of Treatment Volume 100 at the same time.

Calculate Leaf Positions Step 1130 optionally includes both associating beam aperture positions around Gantry 310 and associating different Leaf Pairs 230 with different groups. For example, Calculate Leaf Positions Step 1130 optionally includes dividing Treatment Volume 100 into first through fourth parts, assigning opposing aperture positions to the first part and second part, and also assigning each leaf pair to either the third or the fourth group. This may result in three or four fluence levels.

Calculate Leaf Positions Step 1130 optionally includes determining that the calculated leaf positions can be achieved within mechanical limitations of Beam Aperture 200. For example, Calculate Leaf Positions Step 1130 may include a determination of how quickly Leaves 210 can be moved between the calculated leaf positions.

In a Deliver Radiation Step 1140, radiation is delivered at the plurality of fluence levels to Treatment Volume 100 using the leaf positions calculated in Calculate Leaf Positions Step 1130.

Several embodiments are specifically illustrated and/or described herein. However, it will be appreciated that modifications and variations are covered by the above teachings and within the scope of the appended claims without departing from the spirit and intended scope thereof. For example, while many of the illustrations and examples disclosed herein are in a two-dimensional context, one of ordinary skill in the art will understand that these same illustrations and examples are intended to be applied to the three dimensions actually encountered in radiation therapy. Further, various embodiments of the invention include computing instructions configured to perform various methods and functions described herein, and stored on a computer read readable media. Some embodiments of the invention do not include directly controlling a radiation delivery device. For example, the information produced using the methods discussed herein may be used as a starting point for other algorithms, or can be stored for later used. In these embodiments, Leaf Controller 440 is optional.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The invention claimed is:

1. A radiation treatment system comprising:
    a beam source configured to generate a beam of radiation;
    a beam aperture including a plurality of aperture leaves configured to shape the beam of radiation;
    a gantry configured to move the beam aperture; and
    a computing device configured to control the plurality of aperture leaves so as to provide a plurality of radiation fluence levels to different portions of a treatment volume while the beam aperture is in motion and travels 360 degrees or less around the treatment volume using the gantry.

2. The radiation treatment system of claim 1, wherein the computing device is further configured for calculating a leaf position for each of the plurality of aperture leaves responsive to the plurality of radiation fluence levels.

3. The radiation treatment system of claim 1, wherein the computing device is further configured to control the plurality of aperture leaves so as to provide the plurality of radiation fluence levels by assigning different positions of the beam aperture on the gantry to different groups, each of the different groups being configured to radiate a different part of the treatment volume.

4. The radiation treatment system of claim 1, wherein the computing device is further configured to control the plurality of aperture leaves so as to provide the plurality of radiation fluence levels by using different leaf positioning rules for different groups of leaf pairs.

5. The radiation treatment system of claim 1, wherein the computing device is further configured to control the plurality of aperture leaves so as to provide the plurality of radiation fluence levels by using different leaf positioning rules for different positions of the beam aperture on the gantry.

6. The radiation treatment system of claim 1, wherein the computing device is further configured to determine which parts of the treatment volume should receive radiation using different leaf pairs or from different positions of the beam aperture on the gantry, based on a division line.

7. The radiation treatment system of claim 1, wherein the plurality of radiation fluence levels includes more than two radiation fluence levels.

8. The radiation treatment system of claim 1, wherein controlling the plurality of aperture leaves includes using the plurality of aperture leaves to create two separate openings in the beam aperture at the same time.

9. The radiation treatment system of claim 1, wherein the beam source is an x-ray source.

10. A method of determining a configuration of a radiation treatment system, the method comprising:
receiving a plurality of optimal fluences to be delivered to different portions of the treatment volume, the optimal fluences being configured to provide a desired three-dimensional dose distribution to the treatment volume;
determining a plurality of discrete fluence levels to be delivered to the treatment volume in order to approximately reproduce the optimal fluences; and
calculating leaf positions for each leaf of a beam aperture at each of a plurality of beam aperture positions in order to achieve the plurality of discrete fluence levels while the beam aperture is in motion and travels one or fewer times around an arc of rotation.

11. The method of claim 10, wherein calculating leaf positions for each leaf pair comprises associating a first part of the treatment volume with a first group of beam aperture positions and associating a second part of the treatment volume with a second group of beam aperture positions.

12. The method of claim 11, wherein the leaf pairs are configured to deliver radiation to the first part of the treatment volume at positions associated with the first group and configured to deliver radiation to the second part of the treatment volume at positions associated with the second group.

13. The method of claim 11, wherein a first gantry position associated with the first group is opposite to a second gantry position associated with the second group.

14. The method of claim 11, wherein the plurality of the discrete fluence levels are delivered to the treatment volume in one or fewer rotations of the beam aperture around a gantry without substantial loss of spatial resolution.

15. The method of claim 10, wherein calculating leaf positions for each leaf pair comprises assigning a first leaf pair of the beam aperture to a first group and assigning a second leaf pair of the beam aperture to a second group.

16. The method of claim 15, wherein the first leaf pair is configured to deliver radiation to the first part of the treatment volume and the second leaf pair is configured to deliver radiation to the second part of the treatment volume.

17. The method of claim 16, wherein the first leaf pair and the second leaf pair are configured to deliver radiation to the treatment volume at the same time.

18. The method of claim 10, wherein calculating leaf positions for each leaf pair comprises dividing the treatment volume into at least a first part and a second part using a division line, and associating the first part with a first group and the second part with a second group, the first group and the second group comprising either different positions of the beam aperture or different leaf pairs, respectively.

19. The method of claim 10, further including using a leaf controller to move each leaf pair into the calculated leaf positions at each of the plurality of beam aperture positions, and providing radiation at the plurality of discrete fluence levels to the treatment volume while moving the beam aperture one or fewer times around the arc of rotation.

20. The method of claim 10, wherein calculating leaf positions for each leaf pair comprises:
at each of the plurality of beam source positions, associating a first part of the treatment volume with a first group of beam aperture positions and associating a second part of the treatment volume with a second group of beam aperture positions; and
associating a first group of leaf pairs with a third part of the treatment volume and associating a second group of the leaf pairs with a fourth part of the treatment volume.

21. The method of claim 10, wherein the plurality of discrete fluence levels include more than two fluence levels.

22. The method of claim 10, wherein calculating leaf positions includes determining that the calculated leaf positions can be achieved within mechanical limitations of beam aperture.

23. The method of claim 10, wherein the optimal fluences are continuous.

24. A computing system comprising:
a fluence determination engine configured to determine a plurality of discrete fluence levels to approximate a plurality of optimal fluences;
a leaf position calculator configured to calculate leaf positions for a plurality of leaves in a radiation beam aperture, the leaf positions being configured to provide the plurality of radiation fluence levels to different portions of a treatment volume while the radiation beam aperture is in motion and travels one rotation or less around the treatment volume; and
a leaf controller configured to control the plurality of leaves according to the leaf positions calculated using the leaf position calculator.

25. The computing system of claim 24, wherein the leaf position calculator is configured to calculate the leaf positions by separating leaf pairs into more than one group, each of the more than one group being configured to radiate a different part of the treatment volume.

26. The computing system of claim 24, wherein the leaf position calculator is configured to calculate the leaf positions by dividing positions of the beam aperture into more than one group, each of the more than one group being configured to radiate a different part of the treatment volume.

27. The computing system of claim 24, wherein the leaf position calculator is further configured to calculate leaf positions for the plurality of leaves so as to provide the plurality of radiation fluence levels by assigning different leaves of the plurality of leaves to different groups, each of the different groups being configured to radiate a different part of the treatment volume.

28. The computing system of claim 24, wherein the leaf position calculator is further configured to calculate leaf positions for the plurality of leaves so as to provide the plurality of radiation fluence levels by assigning different leaves of the plurality of aperture leaves to different groups, a first member of the different groups being configured to radiate a first part of the treatment volume and a second member of the different groups being configured to radiate a second part of the treatment volume, the first part of the treatment volume overlapping the second part of the treatment volume.

29. The computing system of claim 24, wherein the leaf position calculator is further configured to determine which parts of the treatment volume should receive radiation using different leaf pairs or from different positions of the beam aperture on the gantry, based on a division line.

30. The computing system of claim 24, wherein the plurality of radiation fluence levels includes more than two radiation fluence levels.

31. The computing system of claim 24, wherein the beam source is an x-ray source.

* * * * *